United States Patent [19]

Hiruta et al.

[11] Patent Number: 5,718,228
[45] Date of Patent: Feb. 17, 1998

[54] ULTRASONIC DIAGNOSTIC APPARATUS

[75] Inventors: Masahiro Hiruta; Nobushi Iwashita, both of Kawasaki, Japan

[73] Assignee: Fujitsu Ltd., Kawasaki, Japan

[21] Appl. No.: 751,314

[22] Filed: Nov. 18, 1996

[30] Foreign Application Priority Data

Mar. 13, 1996 [JP] Japan .................... 8-056368

[51] Int. Cl.$^6$ ........................................ A61B 8/00
[52] U.S. Cl. .......................................... 128/660.04
[58] Field of Search ................. 128/660.01, 662.03, 128/660.1, 662.06, 660.04; 73/683

[56] References Cited

U.S. PATENT DOCUMENTS 5,316,003  5/1994  Stouffer .................. 128/662.03
5,351,692  10/1994  Dow et al. ............... 128/660.1

Primary Examiner—Francis Jaworski
Attorney, Agent, or Firm—Staas & Halsey

[57] ABSTRACT

There is provided an ultrasonic diagnostic apparatus in which ultrasonic waves are transmitted into the subject to obtain received signals through receiving the ultrasonic waves reflected within the subject, thereby displaying an image based on the received signals. In the ultrasonic diagnostic apparatus, a contact or non-contact of the tip portion of the ultrasonic probe with the subject is detected. At the time point when the non-contact is detected, a display mode of a CRT display is changed from a dynamic image mode to a still image mode (a freeze mode), so that a desired image is displayed in the form of a still image.

10 Claims, 5 Drawing Sheets

ULTRASONIC DIAGNOSTIC APPARATUS

BACKGROUND OF THE INVENTION

1. Field of the Invention

The present invention relates to an ultrasonic diagnostic apparatus in which ultrasonic waves are transmitted into the subject to obtain electrical signals through receiving the ultrasonic waves reflected within the subject, thereby visualizing the inside of the subject based on the received signals.

2. Description of the Related Art

There has been generally used an ultrasonic diagnostic apparatus in which images visualizing the inside of the subject, especially, the human body are submitted for a medical diagnosis, on the grounds that such an ultrasonic diagnostic apparatus involves no danger of an exposure different from an X-ray system, and also is non-invasive and simple in operation.

FIG. 3 is a schematic perspective illustration showing one example of an ultrasonic diagnostic apparatus.

In FIG. 3, an ultrasonic diagnostic apparatus 10 is connected through connectors (not illustrated) provided on a main frame 30 to two ultrasonic probes 20 (not illustrated) each having ultrasonic transducers connected through a cable 21 for receiving and transmitting ultrasonic waves and a connector 22 provided at the rear end of the cable 21.

The main frame 30 incorporates thereinto a control circuit for providing such a control that ultrasonic pulses are transmitted in a predetermined timing from the ultrasonic transducers of the tip of the ultrasonic probe 20, and a signal processing circuit for processing the received signals, which are obtained through reflection of the ultrasonic pulses within the subject and conversion of the ultrasonic pulses into electrical signals by the ultrasonic transducers, to form an image signal inside the subject according to the ultrasonic waves. On the top of the main frame 30, there are provided a CRT display 31 for displaying the image thus formed, and an operation panel 32 having switches or the like for giving various instructions to the ultrasonic diagnostic apparatus 10. Further, under portion of the main frame 30, there is provided a caster 33 so that the ultrasonic diagnostic apparatus 10 can move.

FIG. 4 is an illustration useful for understanding an example of use of an ultrasonic diagnostic apparatus according to the related art.

An ultrasonic diagnostic apparatus 10 is disposed near a bed 50. A tip of an ultrasonic probe 20 extending from the ultrasonic diagnostic apparatus 10 is operated by a doctor 52 in a state that the tip is in contact with a patient 51 (the subject) who lies down on the bed 50.

The ultrasonic diagnostic apparatus is basically arranged in the fashion as mentioned above. An image in the body of the patient 51, according to the ultrasonic waves, is displayed on a CRT display 31. The displayed image is useful for a diagnosis of the patient 51. It is often performed that the image displayed on the CRT display 31 is recorded on a video tape or photographed in the form of an instant photograph (Polaroid photograph).

Such an ultrasonic diagnostic apparatus has usually not only a dynamic image mode in which the motion of a tip portion of the ultrasonic probe 20 operated as shown in FIG. 4 and a dynamic image moving on a real time in accordance with a change of a tissue in the body of the patient 51 are displayed, but also a still image mode (a so-called freeze function) in which a still image based on the image signal generated at a predetermined time point is displayed.

The dynamic image mode and the still image mode are alternately switched, for example, whenever a freeze key 32a provided on the operation panel 32 is depressed once. In the state of the dynamic image mode, if the freeze key 32a is depressed, the image at the point of time when the freeze key 32a is depressed is displayed in the form of the still image.

FIG. 5 is a functional block diagram of the ultrasonic diagnostic apparatus having the freeze function. Since the basic structure of the ultrasonic diagnostic apparatus is well known, only the portions necessary for a comparison with the ultrasonic diagnostic apparatus according to the present invention will be described, and the redundant explanation will be omitted.

In FIG. 5, the tip portion 20a of the ultrasonic probe 20 is provided with ultrasonic transducers 23. The ultrasonic transducers 23 are put on a surface of the body of the subject 51 and operated as shown in FIG. 4.

A transmitter and receiver unit 34 produces drive signals to be applied to the ultrasonic transducers 23 on the basis of control by a transmission and receive control 35. The drive signals thus produced cause the ultrasonic transducers 23 to transmit ultrasonic waves into the subject 51. The ultrasonic waves reflected within the subject 51 are received by the ultrasonic transducers 23 to be converted into electrical signals. The electrical signals are received by the transmitter and receiver unit 34 under control of a transmission and receive control unit 35. The signals received by the transmitter and receiver unit 34 are applied to an analog control unit 36 in which the received signals are subjected to an AD conversion through processings for the received signals such as an amplification, a logarithmic amplification, a full wave rectification and a filtering. The digital signals produced in the analog control unit 36 are applied to a digital scan converter (DSC) unit 37 in which the digital image signals are converted into image signals suitable for a display scanning scheme according to a CRT display 31. The image signals for a display, which are produced in the digital scan converter unit 37, are transmitted a display control unit 38 and displayed on the CRT display 31 in accordance with an instruction of a system control unit 39.

The operation panel 32 shown in FIG. 4 is provided with the freeze key 32a. It is detected by a system control unit 39 for controlling the freeze function that the freeze key 32a was depressed.

When the system control unit 39 detects the fact that the freeze key 32a was depressed in the state of the dynamic image mode, the system control unit 39 instructs the transmission and receive control unit 35 to stop transmission and reception of the ultrasonic waves, and in addition instructs the display control unit 38 to stop writing into the frame memory and perform only reading out from the frame memory to display image information.

Thus, the image, which is involved in a time point when the freeze key 32a is depressed, is displayed on the CRT display 31 in the form of a still image. When the freeze key 32a is depressed again, the system control unit 39 instructs the transmission and receive control unit 35 to resume transmission and reception of the ultrasonic waves, and in addition instructs the display control unit 38 to resume writing into and reading out from the frame memory.

As a result, a display of the dynamic image is resumed on the CRT display 31.

In the diagnosis using an ultrasonic diagnostic apparatus, the freeze function is a very useful function in the point such that the image of interest is displayed in the form of a still image for a careful observation, and/or be photographed in the form of an instant photograph (Polaroid photograph).

To utilize the freeze function, as shown in FIG. 4, for example, an operator observes the display screen of the CRT display 31 while operating the tip portion of the ultrasonic probes 20 by his right hand, and at the timing in which the image of interest is displayed, the operator depresses the freeze key 32a by his left hand.

It will happen, however, that the bed 50 is apart little too far from the ultrasonic diagnostic apparatus main frame 30, or the tip portion of the probe 20 is apart little too far from the freeze key 32a as to some portions of the subject 51 to depress the freeze key 32a by the operator's left hand while the tip portion of the probe 20 is held by the operator's right hand. In those situations, if the operator intends to depress the freeze key 32a by his left hand while the tip portion of the probe 20 is held by his right hand, there is the possibility that the operator's right hand moves and as a result an image different from the image of interest is displayed in the form of the still image on the CRT display 31.

For the purpose of solving the above-mentioned problem, there has been proposed an ultrasonic diagnostic apparatus in which the tip portion of an ultrasonic probe 20 is provided with a mechanical freeze switch so that the operator can operate by only his right hand. However, also in this case, the tip portion of an ultrasonic probe 20 inadvertently moves through operation of the freeze switch, and thus there is the possibility that an image different from the image of interest is inadvertently displayed in the form of the still image. In effect, the above-mentioned problem is not yet solved.

SUMMARY OF THE INVENTION

In view of the foregoing, it is therefore an object of the present invention to provide an ultrasonic diagnostic apparatus capable of displaying an intended still image from dynamic images.

To achieve the above-mentioned objects, according to the present invention, there is provided an ultrasonic diagnostic apparatus comprising:

an ultrasonic probe having on a tip portion thereof ultrasonic transducers each, upon receipt of a predetermined drive electrical signal, for transmitting ultrasonic waves inside a subject and receiving the ultrasonic waves reflected within the subject to form electrical signals, and a cable adapted for transmitting the drive electrical signals and the received electrical signals; and a main block comprising a transmitter and receiver unit for generating the drive electrical signals to drive said ultrasonic transducers so as to transmit the ultrasonic waves, receiving the received electrical signals formed by said ultrasonic transducers, and applying an analog processing to the received electrical signals, a transmission and receive control unit for controlling said transmitter and receiver unit, an image signal generating unit for producing image signals to visualize inside of the subject in accordance with signals outputted from said transmitter and receiver unit, and an image display unit for displaying an image based on the image signals produced by said image signal generating unit, said ultrasonic diagnostic apparatus further comprising:

an image control unit selectively operative in a mode between a dynamic image mode in which the image signals produced in turn in said image signal generating unit are sequentially transmitted to said image display unit, so that the image signals sequentially transmitted are displayed on said image display unit in form of a dynamic image, and a still image mode in which the image signals produced at a predetermined time in said image signal generating unit are transmitted to said image display unit, so that the image signals sequentially transmitted are displayed on said image display unit in form of a still image; and a mode selection unit for selecting said image control unit in a mode between the dynamic image mode and the still image mode in accordance with a mutual action between the tip portion of said ultrasonic probe and the subject.

According to the apparatus of the present invention, the mode selection unit selects the image control unit in a mode between the dynamic image mode and the still image mode in accordance with a mutual action between the tip portion of said ultrasonic probe and the subject. Thus, it is very excellent in operability with respect to the freeze function, and it is possible to display a desired image in the form of a still image with a simple operation.

Here, it is noted that the term "mutual action" is not restricted to a particular meaning. It is possible to adopt, for example, a contact or non-contact of the tip portion of the ultrasonic probe with the subject, a pressure or pressure change on the tip portion of the ultrasonic probe by the subject, a velocity of motion of the tip portion of the ultrasonic probe with respect to the subject, and the combination of these items as the mutual action.

In the apparatus as mentioned above, it is acceptable that the tip portion of said ultrasonic probe is provided with a sensor for detecting the mutual action between the tip portion of said ultrasonic probe and the subject, and said mode selection unit selects said image control unit in a mode between the dynamic image mode and the still image mode in accordance with information obtained by said sensor. Further, it is also acceptable that said mode selection unit has a detection unit for detecting the mutual action between the tip portion of said ultrasonic probe and the subject in accordance with the received signals obtained by said ultrasonic transducers, and said mode selection unit selects said image control unit in a mode between the dynamic image mode and the still image mode in accordance with information obtained by said detection unit.

As mentioned above, while the term "mutual action" referred to in the present invention is not restricted to the particular mutual action, typically, it is preferable that said mode selection unit adopts a phenomenon as to whether the tip portion of said ultrasonic probe is in contact with the subject, as the mutual action, and when the tip portion of said ultrasonic probe is in contact with the subject, said mode selection unit selects said image control unit in the mode, while when the tip portion of said ultrasonic probe detaches from the subject, said mode selection unit selects said image control unit in the still image mode.

Further, it is also preferable that said image control unit has an image memory for storing an image signal produced a predetermined time before an image signal involved in an image now displayed on said image display unit was produced in the dynamic image mode, and when the still image mode is selected in accordance with an instruction of the mode selection unit, said image control unit feeds the image signal stored in said image memory to said image display unit.

In some mutual action, it is considered that when an occurrence of a phenomenon that the mode is to be switched from the dynamic image mode to the still image mode is detected, time has elapsed as compared with the timing in which the mode is to be switched to the still image mode. In view of this point, the image memory as mentioned above is used to store an image signal involved in the time by the corresponding time elapsed before such a timing. When the phenomenon that the mode is to be switched to the still image mode is detected, the still image is displayed on the basis of the image signal stored in the image memory. Thus, it is possible to compensate for the time lag.

DESCRIPTION OF THE PREFERRED EMBODIMENTS

Hereinafter, there will be described embodiments of the present invention.

Figure 1:
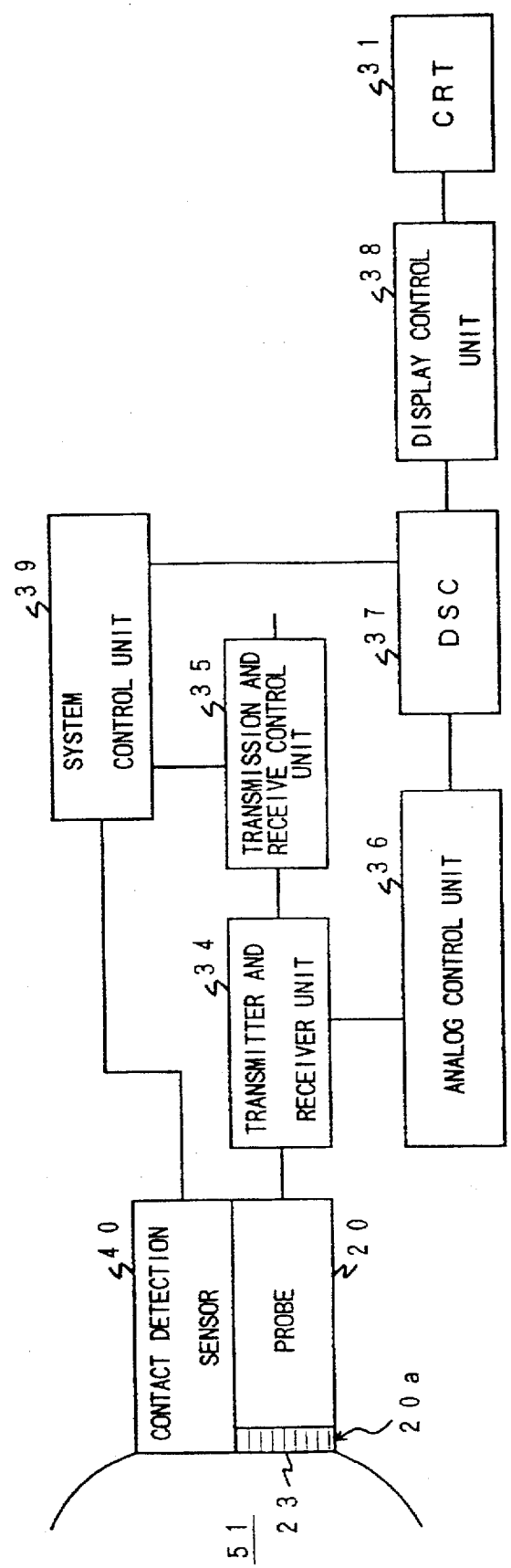
FIG. 1 is a functional block diagram of an ultrasonic diagnostic apparatus according to the first embodiment of the present invention.
Figure 5:
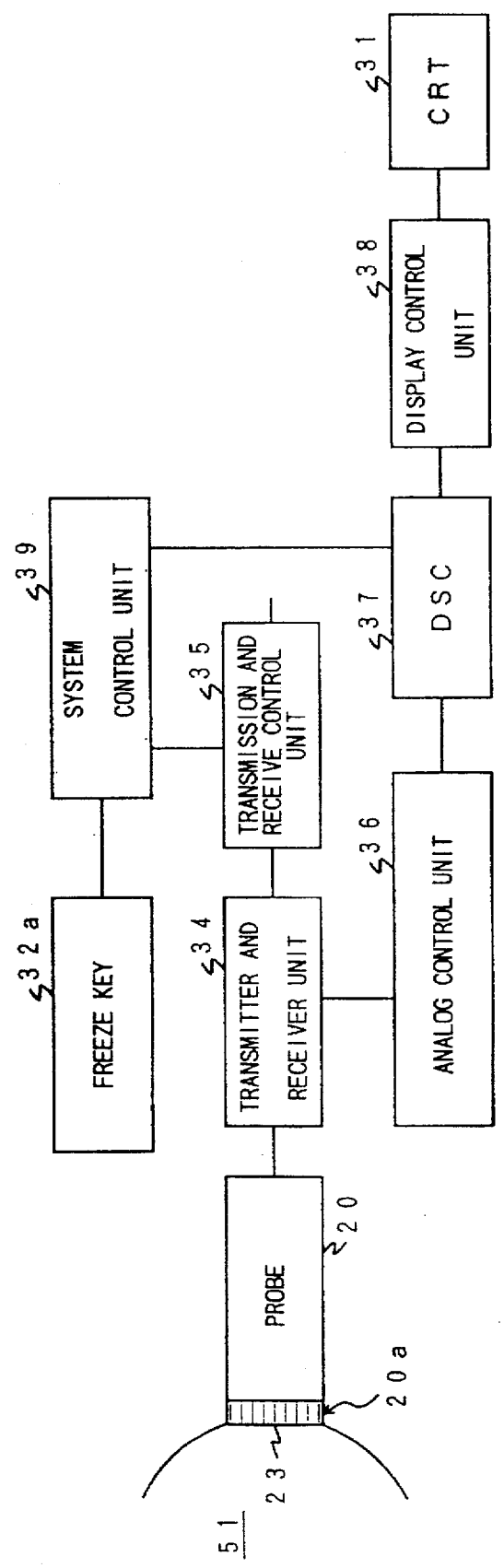
FIG. 5 is a functional block diagram of the ultrasonic diagnostic apparatus having a freeze function.

FIG. 1 is a functional block diagram of an ultrasonic diagnostic apparatus according to the first embodiment of the present invention. There will be described points different from the ultrasonic diagnostic apparatus shown in FIG. 5.

According to the ultrasonic diagnostic apparatus shown in FIG. 1, the tip portion 20a of an ultrasonic probe 20 is provided with a contact detection sensor 40 for detecting whether the tip portion 20a is in contact with a subject 51. As to the contact detection sensor 40, any types of sensors are available, as far as it can detect the contact or the non-contact, for example, a mechanical sensor involving a mechanical movement, a photoelectric sensor, a pressure sensor, a thermosensitive sensor and the like. Information as to the contact or the non-contact, which is obtained through the contact detection sensor 40, is transferred to a system control unit 39. Upon receipt of such information, the system control unit 39 instructs a transmission and receive control unit 35, a digital scan converter (DSC) unit 37 and a display control unit 38 to provide such a control that when the situation is changed from the contact to the non-contact, the mode is switched to a freeze state (still image mode), on the other hand, when the situation is changed from the non-contact to the contact, the mode is switched to a dynamic image mode.

Figure 4:
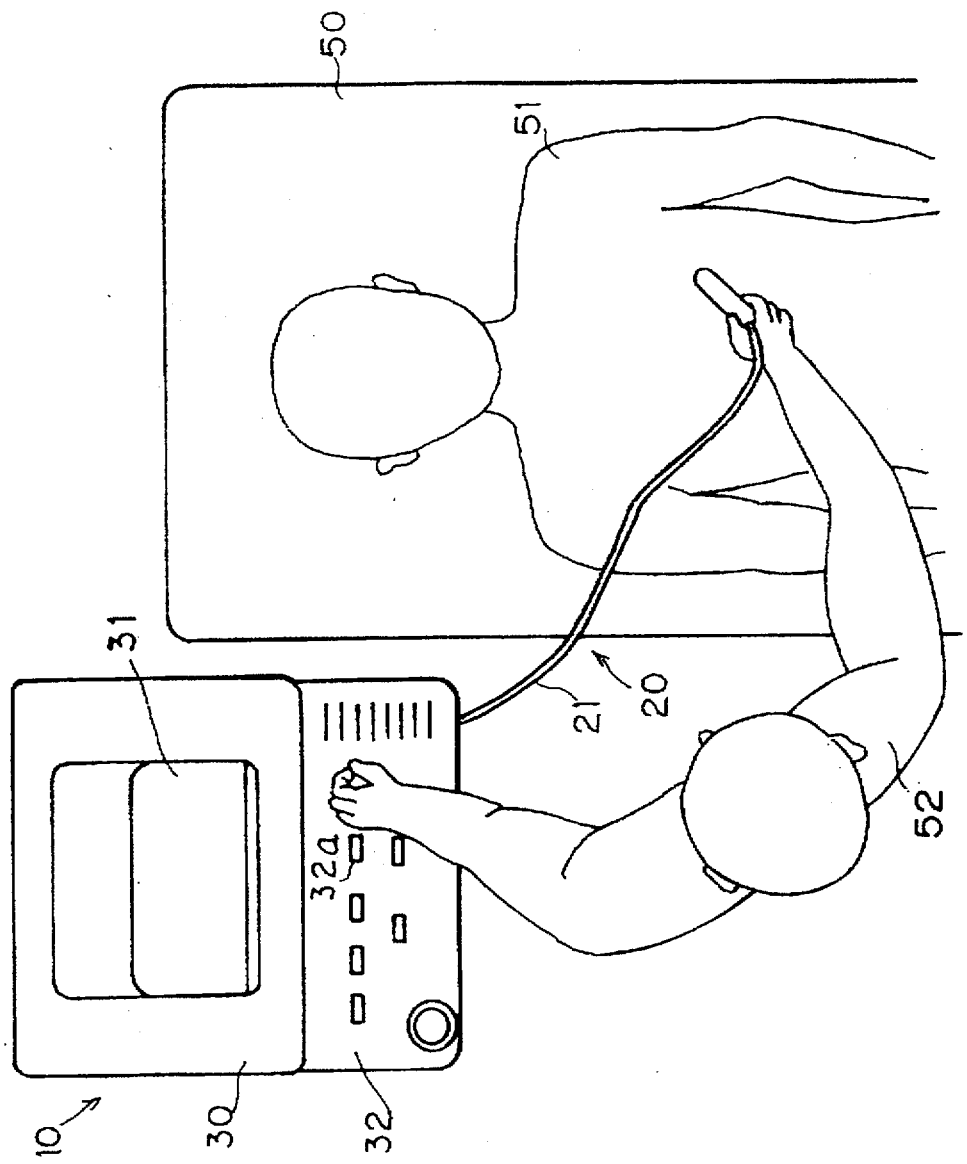
FIG. 4 is an illustration useful for understanding an example of use of an ultrasonic diagnostic apparatus according to the related art.

Consequently, it is sufficient for an operator of the ultrasonic diagnostic apparatus to operate the tip portion of the ultrasonic probe 20, as shown in FIG. 4, and to detach the tip portion of the ultrasonic probe 20 from a body surface of the subject 51 when the picture image of interest is displayed on the CRT display 31. This performance is very excellent in an operability when the freeze function is utilized. Thus, it is possible to display on the CRT display 31 a desired picture image in the form of a still image with a simple operation.

Figure 2:
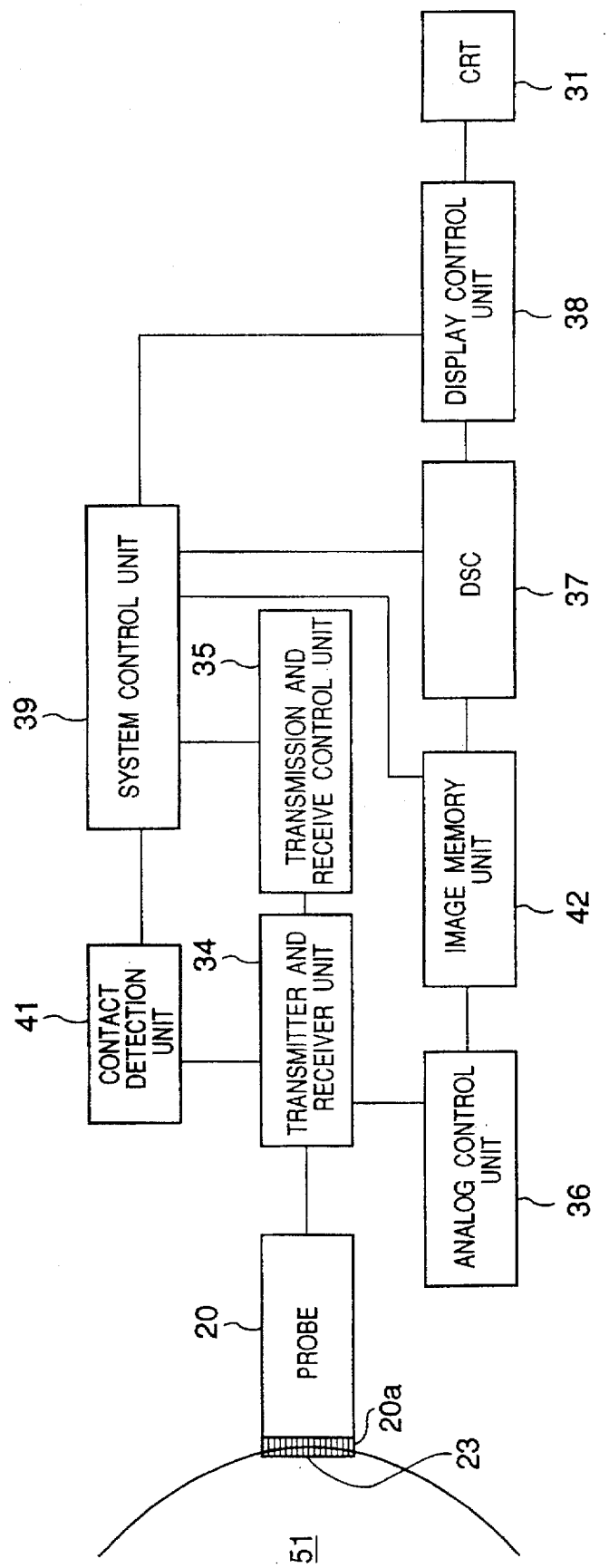
FIG. 2 is a functional block diagram of an ultrasonic diagnostic apparatus according to the second embodiment of the present invention.
Figure 3:
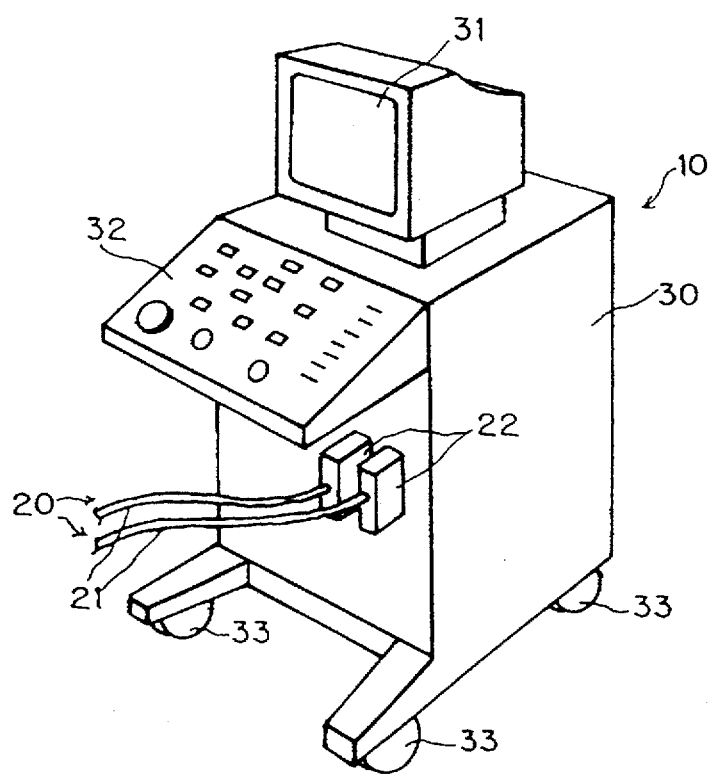
FIG. 3 is a schematic perspective view of an ultrasonic diagnostic apparatus by way of example.

FIG. 2 is a functional block diagram of an ultrasonic diagnostic apparatus according to the second embodiment of the present invention. Hereinafter, there will be described points different from the ultrasonic diagnostic apparatus shown in FIG. 1.

According to the ultrasonic diagnostic apparatus shown in FIG. 2, the tip portion of an ultrasonic probe 20 is provided with no sensor but the ultrasonic transducers 23. The contact or non-contact of the tip portion 20a of the ultrasonic probe 20 with the subject 51 is detected by utilizing such a phenomenon that the received signals, which are formed through receiving the reflected ultrasonic waves by the ultrasonic transducers 23, are varied depending on whether the tip portion 20a of the ultrasonic probe 20 is in contact with the subject 51. Specifically, according to the ultrasonic diagnostic apparatus shown in FIG. 2, there is provided a contact detection unit 41 for detecting whether the tip portion 20a of the ultrasonic probe 20 is in contact with the subject 51.

Further, the ultrasonic diagnostic apparatus shown in FIG. 2 has an image memory unit 42. Strictly speaking, there occurs a little time lag (several tens of m seconds) from the time an image, which is attempted to be observed in the form of a still image, is displayed on the CRT display 31, until an operator detaches the tip portion 20a of the ultrasonic probe 20 from the subject 51, the non-contact is detected by the contact detection unit 41, and the mode is switched to the still image mode. In order to compensate for such a little time lag, there is provided the image memory unit 42 for storing an image signal generated in an analog control unit 36. This image signal was produced by the analog control unit 36 at the time before by the corresponding time lag mentioned above as compared with the time when the image signal on the basis of which the current image is displayed on the CRT display 31 is produced in the dynamic image mode.

In this condition, when the mode is switched to the still mode, the image signal produced at the time before by the corresponding time lag mentioned above, which is stored in the image memory unit 42 at that time, is transferred to the digital scan converter unit (DSC) 37 to be converted into an image signal for a display, so that the still image is displayed on the CRT display 31 under control of a display control unit 38. Thus, the image, which an operator attempts to observe in the form of a still image, is displayed on the CRT display 31.

Incidentally, since the ultrasonic diagnostic apparatus shown in FIG. 2 is to detect the contact or non-contact on the basis of the received signals formed through receiving the ultrasonic waves, there is performed transmission and receiving of the ultrasonic waves even in the still image mode wherein the tip portion 20a of the ultrasonic probe 20 is detached from the subject 51. Consequently, the system control unit 39 gives in any modes of the dynamic image mode and the still image mode instructions for transmission and receiving to the transmission and receive control unit 35, but gives to the digital scan converter (DSC) unit 37, the image memory unit 42 and the display control unit 38 instructions according to the dynamic image mode and the still image mode.

As to the transmission and receiving of ultrasonic waves in the still image mode, it is acceptable that the interval of the transmission and receiving of ultrasonic waves is spread in such an extent that a change from the non-contact to the contact can be detected without a delay.

According to the above-mentioned respective embodiments of the present invention, the mode is switched through detecting the contact or the non-contact of the tip portion 20a of the ultrasonic probe 20 with the subject 51. However, as mentioned above, according to the present invention, there is no need to detect the contact or the non-contact, and it is acceptable to perform a selection of the mode on the basis of any types of mutual action such as a contact pressure or a contact pressure change, a temperature change, a velocity of motion of the tip portion of the ultrasonic probe and the like.

As described above, according to the present invention, It is very excellent in an operability when the freeze function is utilized. Thus, it is possible to observe a desired image in the form of a still image with a simple operation.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

We claim:

1. An ultrasonic diagnostic apparatus comprising:

an ultrasonic probe having on a tip portion thereof ultrasonic transducers each, upon receipt of a predetermined drive electrical signal, for transmitting ultrasonic waves inside a subject and receiving the ultrasonic waves reflected within the subject to form electrical signals, and a cable adapted for transmitting the drive electrical signals and the received electrical signals, the tip portion of the ultrasonic probe interacting with the subject in a mutual action;

a main block comprising a transmitter and receiver unit for generating the drive electrical signals to drive said ultrasonic transducers so as to transmit the ultrasonic waves, receiving the received electrical signals formed by said ultrasonic transducers, and applying an analog processing to the received electrical signals, a transmission and receive control unit for controlling said transmitter and receiver unit, an image signal generating unit for producing image signals to visualize inside of the subject in accordance with signals outputted from said transmitter and receiver unit, and an image display unit for displaying an image based on the image signals produced by said image signal generating unit;

an image control unit selectively operative in a mode between a dynamic image mode in which the image signals produced in turn in said image signal generating unit are sequentially transmitted to said image display unit, so that the image signals sequentially transmitted are displayed on said image display unit in form of a dynamic image, and a still image mode in which the image signals produced at a predetermined time in said image signal generating unit are transmitted to said image display unit, so that the image signals sequentially transmitted are displayed on said image display unit in form of a still image; and a mode selection unit for selecting the mode of said image control unit between the dynamic image mode and the still image mode in accordance with the mutual action between the tip portion of said ultrasonic probe and the subject, the tip portion of said ultrasonic probe is provided with a sensor for detecting the mutual action between the tip portion of said ultrasonic probe and the subject, and said mode selection unit selects said image control unit in a mode between the dynamic image mode and the still image mode in accordance with information obtained by said sensor.

2. An apparatus according to claim 1, wherein said image control unit has an image memory for storing an image signal produced a predetermined time before an image signal involved in an image now displayed on said image display unit was produced in the dynamic image mode, and when the still image mode is selected, said image control unit feeds the image signal stored in said image memory to said image display unit.

3. An apparatus according to claim 1, wherein the mode selection units selects between the dynamic image mode and the still image mode in accordance with a pressure between the tip portion of the ultrasonic probe and the subject, as the mutual action.

4. An apparatus according to claim 1, wherein the mode selection unit selects between the dynamic image mode and the still image mode in accordance with a velocity of the tip portion of the ultrasonic probe with respect to the subject, as the mutual action.

5. An ultrasonic diagnostic apparatus comprising:

an ultrasonic probe having on a tip portion thereof ultrasonic transducers each, upon receipt of a predetermined drive electrical signal, for transmitting ultrasonic waves inside a subject and receiving the ultrasonic waves reflected within the subject to form electrical signals, and a cable adapted for transmitting the drive electrical signals and the received electrical signals, the tip portion of the ultrasonic probe interacting with the subject in a mutual action;

a main block comprising a transmitter and receiver unit for generating the drive electrical signals to drive said ultrasonic transducers so as to transmit the ultrasonic waves, receiving the received electrical signals formed by said ultrasonic transducers, and applying an analog processing to the received electrical signals, a transmission and receive control unit for controlling said transmitter and receiver unit, an image signal generating unit for producing image signals to visualize inside of the subject in accordance with signals outputted from said transmitter and receiver unit, and an image display unit for displaying an image based on the image signals produced by said image signal generating unit;

an image control unit selectively operative in a mode between a dynamic image mode in which the image signals produced in turn in said image signal generating unit are sequentially transmitted to said image display unit, so that the image signals sequentially transmitted are displayed on said image display unit in form of a dynamic image, and a still image mode in which the image signals produced at a predetermined time in said image signal generating unit are transmitted to said image display unit, so that the image signals sequentially transmitted are displayed on said image display unit in form of a still image; and a mode selection unit for selecting the mode of said image control unit between the dynamic image mode and the still image mode in accordance with the mutual action between the tip portion of said ultrasonic probe and the subject, said mode selection unit has a detection unit for detecting the mutual action between the tip portion of said ultrasonic probe and the subject in accordance with the received signals obtained by said ultrasonic transducers, and said mode selection unit selects said image control unit in a mode between the dynamic image mode and the still image mode in accordance with information obtained by said detection unit.

6. An apparatus according to claim 5, wherein said image control unit has an image memory for storing an image signal produced a predetermined time before an image signal involved in an image now displayed on said image display unit was produced in the dynamic image mode, and when the still image mode is selected, said image control unit feeds the image signal stored in said image memory to said image display unit.

7. An apparatus according to claim 5, wherein the mode selection units selects between the dynamic image mode and the still image mode in accordance with a pressure between the tip portion of the ultrasonic probe and the subject, as the mutual action.

8. An apparatus according to claim 5, wherein the mode selection unit selects between the dynamic image mode and the still image mode in accordance with a velocity of the tip portion of the ultrasonic probe with respect to the subject, as the mutual action.

9. An ultrasonic diagnostic apparatus comprising:

an ultrasonic probe having on a tip portion thereof ultrasonic transducers each, upon receipt of predetermined drive electrical signal, for transmitting ultrasonic waves inside a subject and receiving the ultrasonic waves reflected within the subject to form electrical signals, and a cable adapted for transmitting the drive electrical signals and the received electrical signals;

a main block comprising a transmitter and receiver unit for generating the drive electrical signals to drive said ultrasonic transducers so as to transmit the ultrasonic waves, receiving the received electrical signals formed by said ultrasonic transducers, and applying an analog processing to the received electrical signals, a transmission and receive control unit for controlling said transmitter and receiver unit, an image signal generating unit for producing image signals to visualize inside of the subject in accordance with signals outputted from said transmitter and receiver unit, and an image display unit for displaying an image based on the image signals produced by said image signal generating unit;

an image control unit selectively operative in a mode between a dynamic image mode in which the image signals produced in turn in said image signal generating unit are sequentially transmitted to said image display unit, so that the image signals sequentially transmitted are displayed on said image display unit in form of a dynamic image, and a still image mode in which the image signals produced at a predetermined time in said image signal generating unit are transmitted to said image display unit, so that the image signals sequentially transmitted are displayed on said image display unit in form of a still image; and a mode selection unit for selecting the mode of said image control unit between the dynamic image mode and the still image mode in accordance with whether the tip portion of said ultrasonic probe is in contact with the subject, and when the tip portion of said ultrasonic probe is in contact with the subject, said mode selection unit selects said image control unit in the dynamic image mode, while when the tip portion of said ultrasonic probe detaches from the subject, said mode selection unit selects said image control unit in the still image mode.

10. An apparatus according to claim 9, wherein said image control unit has an image memory for storing an image signal produced a predetermined time before an image signal involved in an image now displayed on said image display unit was produced in the dynamic image mode, and when the still image mode is selected, said image control unit feeds the image signal stored in said image memory to said image display unit.

* * * * *